United States Patent
Mishra

(10) Patent No.: US 10,356,542 B2
(45) Date of Patent: Jul. 16, 2019

(54) AUDITORY PROSTHESIS SYSTEM INCLUDING SOUND PROCESSOR APPARATUS WITH POSITION SENSOR

(71) Applicant: ADVANCED BIONICS AG, Staefa (CH)

(72) Inventor: Lakshmi N. Mishra, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 227 days.

(21) Appl. No.: 15/313,907

(22) PCT Filed: May 28, 2014

(86) PCT No.: PCT/US2014/039822
§ 371 (c)(1),
(2) Date: Nov. 23, 2016

(87) PCT Pub. No.: WO2015/183263
PCT Pub. Date: Dec. 3, 2015

(65) Prior Publication Data
US 2017/0143962 A1  May 25, 2017

(51) Int. Cl.
*A61N 1/36* (2006.01)
*H04R 29/00* (2006.01)
*A61N 1/05* (2006.01)
*A61N 1/372* (2006.01)
*G06F 1/16* (2006.01)
(Continued)

(52) U.S. Cl.
CPC ......... *H04R 29/004* (2013.01); *A61N 1/0541* (2013.01); *A61N 1/36036* (2017.08); *A61N 1/37211* (2013.01); *G06F 1/1694* (2013.01); *H04R 3/005* (2013.01); *H04R 25/505* (2013.01); *H04R 25/606* (2013.01); *H04R 25/70* (2013.01); *H04R 2225/61* (2013.01)

(58) Field of Classification Search
CPC ............ A61N 1/36036; A61N 1/36038; H04R 2225/61; H04R 29/004–006; H04R 25/407
See application file for complete search history.

(56) References Cited

U.S. PATENT DOCUMENTS

| 4,467,145 A | 8/1984 | Borstel |
| 4,955,729 A | 9/1990 | Marx |
| 5,553,152 A | 9/1996 | Newton |
| 5,659,621 A | 8/1997 | Newton |

(Continued)

FOREIGN PATENT DOCUMENTS

| EP | 1585367 | 10/2005 |
| EP | 2071874 | 6/2009 |

(Continued)

*Primary Examiner* — George R Evanisko
(74) *Attorney, Agent, or Firm* — ALG Intellectual Property, LLC

(57) ABSTRACT

An exemplary auditory prosthesis system includes a sound processor apparatus that is configured for external use by a patient and includes 1) a position sensor that detects a positioning of the sound processor apparatus and 2) a control module that is communicatively coupled to the position sensor and performs a predetermined action with respect to the auditory prosthesis system in accordance with the detected positioning of the sound processor apparatus. Corresponding auditory prosthesis systems and methods are also described.

16 Claims, 8 Drawing Sheets

(51) Int. Cl.
*H04R 25/00* (2006.01)
*H04R 3/00* (2006.01)

(56) References Cited

U.S. PATENT DOCUMENTS

| | | | |
|---|---|---|---|
| 6,138,681 A | 10/2000 | Chen et al. | |
| 6,920,229 B2 | 7/2005 | Boesen | |
| 7,529,587 B2 | 5/2009 | Single | |
| 7,561,708 B2 | 7/2009 | Rohrlein | |
| 7,751,898 B2 | 7/2010 | Ibrahim et al. | |
| 8,233,651 B1 | 7/2012 | Haller | |
| 8,315,706 B2 | 11/2012 | Single | |
| 8,401,178 B2 | 3/2013 | Chen et al. | |
| 8,478,416 B2 | 7/2013 | Zierhofer | |
| 8,989,413 B2 | 3/2015 | Ridler et al. | |
| 2005/0033383 A1 | 2/2005 | Ibrahim et al. | |
| 2005/0078846 A1* | 4/2005 | Single | A61N 1/08 381/326 |
| 2005/0226446 A1 | 10/2005 | Luo et al. | |
| 2006/0013420 A1* | 1/2006 | Sacha | H04R 25/43 381/312 |
| 2006/0271199 A1 | 11/2006 | Johnson | |
| 2007/0016267 A1* | 1/2007 | Griffin | A61N 1/36032 607/57 |
| 2007/0230712 A1 | 10/2007 | Belt et al. | |
| 2008/0085023 A1 | 4/2008 | Kulkarni et al. | |
| 2011/0112607 A1 | 5/2011 | Zierhofer | |
| 2012/0197345 A1* | 8/2012 | Staller | A61B 5/7475 607/57 |
| 2013/0064404 A1* | 3/2013 | Ridler | H04R 25/405 381/313 |
| 2013/0079846 A1 | 3/2013 | Single | |
| 2013/0308807 A1 | 11/2013 | Burns | |
| 2015/0281852 A1* | 10/2015 | Sacha | H04R 25/30 381/331 |

FOREIGN PATENT DOCUMENTS

| | | |
|---|---|---|
| EP | 2908549 | 8/2015 |
| WO | WO-2008/127316 | 10/2008 |
| WO | WO-2010/039437 | 4/2010 |
| WO | WO-2011/059970 | 5/2011 |

* cited by examiner

AUDITORY PROSTHESIS SYSTEM INCLUDING SOUND PROCESSOR APPARATUS WITH POSITION SENSOR

BACKGROUND INFORMATION

Many auditory prosthesis systems are capable of implementing a variety of operating modes and/or configurations to assist patients with hearing loss. For example, an auditory prosthesis system may include a sound processor apparatus located external to a patient. In one example, the patient may attempt to modify the operating mode and/or configuration of the sound processor apparatus to achieve better performance and/or additional comfort during a particular activity (e.g., when playing a sport, talking on a telephone, or lying down to sleep). Additionally or alternatively, the patient may attempt to modify the operating mode and/or configuration of the sound processor apparatus to preserve battery life.

In some cases, the patient may encounter certain inconveniences and/or obstacles that limit his or her ability to modify the operating mode and/or configuration of the sound processor apparatus. For example, the sound processor apparatus may include a limited number of user interfaces (e.g., buttons or feedback devices) due at least in part to the apparatus's relatively small size. As a result, the patient may have difficulty utilizing such user interfaces to modify the operating mode and/or configuration of the sound processor apparatus. As another example, the patient may follow a religious practice that restricts him or her from turning on or off electrical devices on a designated day of rest (e.g., Judaism's Shabbat). Additionally or alternatively, the patient may be entirely unaware that a modification to the operating mode and/or configuration of the sound processor apparatus could potentially improve performance and/or provide additional comfort.

Unfortunately, conventional technologies may lack the ability to sense the patient's intent or desire to modify the operating mode and/or configuration of the sound processor apparatus without deliberate user input. Similarly, conventional technologies may lack the ability to sense certain scenarios in which a modification to the operating mode and/or configuration of the sound processor apparatus could potentially improve performance and/or provide additional comfort.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
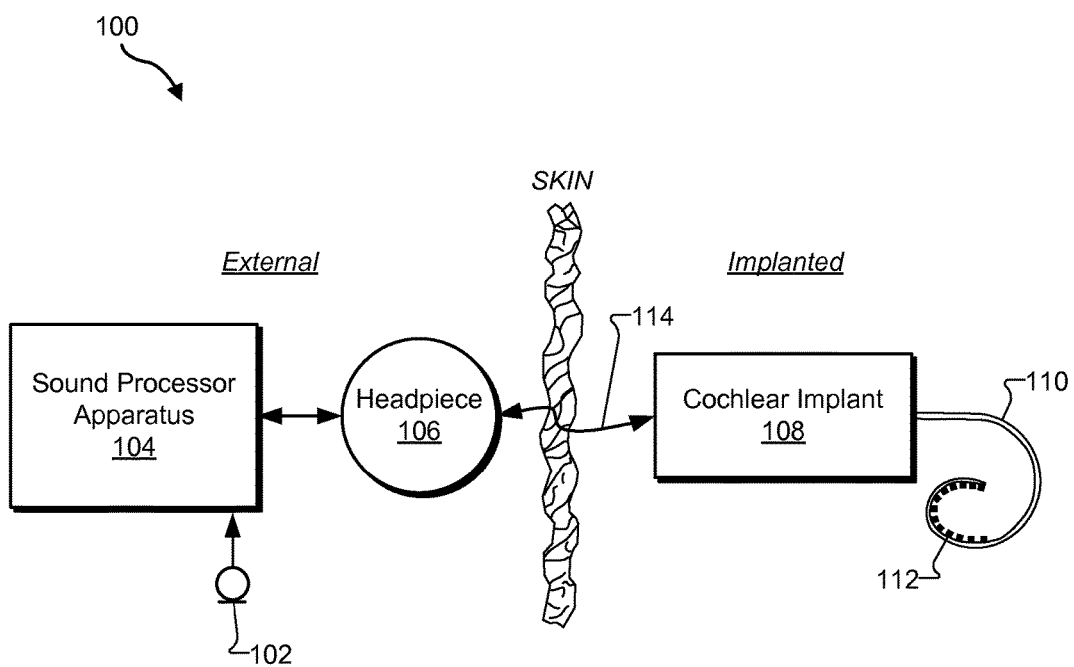
FIG. 1 illustrates an exemplary auditory prosthesis system according to principles described herein.

Auditory prosthesis systems are described herein. As will be described below, an exemplary auditory prosthesis system may include a sound processor apparatus configured for external use by a patient and that includes 1) a position sensor (e.g., a magnetometer, an accelerometer, and/or a gyroscope) that detects a positioning of the sound processor apparatus and 2) a control module that is communicatively coupled to the position sensor and performs a predetermined action with respect to the auditory prosthesis system in accordance with the detected positioning of the sound processor apparatus.

To illustrate, the position sensor may take a measurement used to determine the positioning of the sound processor apparatus. As part of taking this measurement, the position sensor may generate positioning data representative of the positioning of the sound processor apparatus. The position sensor may then provide the positioning data to the control module. Upon receiving the positioning data from the position sensor, the control module may use the positioning data to determine whether the sound processor apparatus has experienced a change in position. For example, the control module may determine that the sound processor apparatus has moved from one position to another and/or experienced a change in orientation.

By using the positioning data to determine whether the sound processor apparatus has experienced a change in position, the control module may enable the sound processor apparatus and/or one or more other components of the auditory prosthesis system to provide the patient with various benefits. For example, the control module may be able to deduce, infer, and/or anticipate the patient's intent or desire to modify an operating mode and/or a configuration of the sound processor apparatus (even without deliberate user input) based at least in part on the positioning data. Additionally or alternatively, the control module may be able to detect and/or anticipate certain scenarios in which a modification to the operating mode and/or configuration of the sound processor apparatus could potentially improve performance and/or provide additional comfort based at least in part on the positioning data.

As an example, the control module may compare the positioning data with reference data representative of a preferred positioning and/or a previous positioning of the sound processor apparatus. The control module may then determine a difference between the preferred and/or previous positioning and the detected positioning based at least in part on the reference data and the positioning data. In response to this determination, the control module may perform a predetermined action with respect to the auditory prosthesis system. Exemplary predetermined actions include, but are not limited to, adjusting a configuration of one or more components (e.g., a beamforming feature) of the auditory prosthesis system, turning the sound processor apparatus on or off, switching active microphones on the auditory prosthesis system, and/or implementing or exiting an operating mode (e.g., a telephone mode, an idle mode, and/or an active mode).

Accordingly, and as will be described in more detail below, the control module and the position sensor may operate in conjunction with each other to improve the performance of the auditory prosthesis system and/or provide additional comfort and/or convenience to the patient, thereby enhancing the patient's overall experience with the auditory prosthesis system.

FIG. 1 illustrates an exemplary auditory prosthesis system 100. As shown, auditory prosthesis system 100 may include various components configured to be located external to a patient including, but not limited to, a microphone 102, a sound processor apparatus 104, and a headpiece 106. Auditory prosthesis system 100 may further include various components configured to be implanted within the patient including, but not limited to, a cochlear implant 108 and a lead 110 with a plurality of electrodes 112 disposed thereon. As will be described in more detail below, additional or alternative components may be included within auditory prosthesis system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include and/or represent a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor apparatus 104. Additionally or alternatively, microphone 102 may be implemented by one or more microphones disposed within headpiece 106, one or more microphones disposed within sound processor apparatus 104, and/or any other suitable microphone as may serve a particular implementation.

Sound processor apparatus 104 (i.e., one or more components included within sound processor apparatus 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor apparatus 104 may process the one or more audio signals in accordance with a selected sound processing strategy or program to generate appropriate stimulation parameters for controlling cochlear implant 108. Sound processor apparatus 104 may include or be implemented by a behind-the-ear ("BTE") unit, a body worn device, and/or any other sound processing unit as may serve a particular implementation.

In some examples, sound processor apparatus 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that wireless communication link 114 may include a bi-directional communication link and/or one or more dedicated uni-directional communication links.

Headpiece 106 may be communicatively coupled to sound processor apparatus 104 and may include an external antenna (e.g., a coil and/or one or more wireless communication components) configured to facilitate selective wireless coupling of sound processor apparatus 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor apparatus 104 and cochlear implant 108 via a wireless communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor apparatus 104 (e.g., an audio signal detected by microphone 102) in accordance with one or more stimulation parameters transmitted thereto by sound processor apparatus 104. Cochlear implant 108 may be further configured to apply the electrical stimulation to one or more stimulation sites within the patient via one or more electrodes 112 disposed along lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

The auditory prosthesis system 100 illustrated in FIG. 1 may be referred to as a cochlear implant system because sound processor apparatus 104 is configured to direct cochlear implant 108 to generate and apply electrical stimulation representative of audio content (e.g., one or more audio signals) to one or more stimulation sites within the patient by way of one or more of electrodes 112. Auditory prosthesis system 100 may alternatively be implemented by an electro-acoustic stimulation ("EAS") system configured to provide both electrical stimulation by way of cochlear implant 108 and acoustic stimulation by way of a receiver or loudspeaker (not shown) connected to sound processor apparatus 104.

Figure 2:
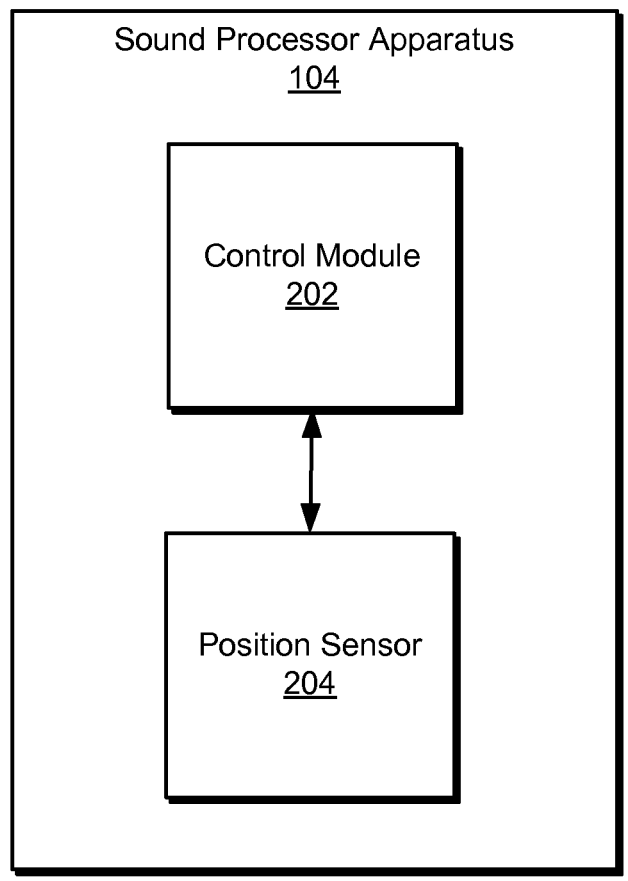
FIG. 2 illustrates exemplary components that may be included within a sound processor apparatus according to principles described herein.

FIG. 2 illustrates exemplary components that may be included within sound processor apparatus 104. As shown, sound processor apparatus 104 may include a control module 202 and a position sensor 204. It will be recognized that sound processor apparatus 104 may include additional or alternative components as may serve a particular implementation. In some examples, one or more of the components included in sound processor apparatus 104 (e.g., control module 202 and position sensor 204) may be housed within a single casing.

Control module 202 may be configured to perform one or more operations with respect to one or more components connected to or otherwise communicatively coupled to sound processor apparatus 104. For example, control module 202 may be configured to control an operation of cochlear implant 108, a receiver (i.e., loudspeaker) connected to sound processor apparatus 104, and/or any other device associated with providing electrical and/or acoustic stimulation to a patient. To illustrate, control module 202 may process an audio signal presented to the patient, generate one or more stimulation parameters based on the processing of the audio signal, and direct cochlear implant 108 to generate and apply electrical stimulation representative of the audio signal to the patient in accordance with the stimulation parameters (e.g., by transmitting the stimulation parameters to cochlear implant 108).

Control module 202 may be additionally or alternatively configured to interact with and/or receive positioning data from position sensor 204 included within sound processor apparatus 104. Control module 202 may be able to deduce, infer, and/or anticipate the patient's intent or desire to modify an operating mode and/or a configuration of the sound processor apparatus (even without deliberate user input) based at least in part on the positioning data. Additionally or alternatively, control module 202 may be able to detect and/or anticipate certain scenarios in which a modification to the operating mode and/or configuration of the sound processor apparatus could potentially improve performance and/or provide additional comfort to the patient based at least in part on the positioning data. Exemplary ways in which these operations may be performed will be described below.

Control module 202 may be implemented by any suitable combination of integrated circuits, circuitry, processors, and/or computing devices configured to perform one or more of the operations and/or functions described herein. Exemplary implementations of control module 202 will be described below.

Position sensor 204 may be configured to take measurements used to determine the positioning of sound processor apparatus 104. To this end, position sensor 204 may include and/or represent any type of form of sensor capable of taking such measurements as may serve a particular implementation. For example, position sensor 204 may include and/or represent a magnetometer, an accelerometer, and/or a gyroscope.

Accordingly, position sensor 204 may take any type or form of measurement used to determine the positioning of sound processor apparatus 104 as may serve a particular implementation. For example, position sensor 204 may detect and/or measure any magnetic activity of sound processor apparatus 104, angular momentum of sound processor apparatus 104, movement of sound processor apparatus 104, or lack thereof. In addition, position sensor 204 may generate positioning data representative of such magnetic activity, angular momentum, and/or movement. Exemplary ways in which these measurements may be used to determine the positioning of sound processor apparatus 104 will be described below.

Control module 202 and position sensor 204 may be implemented in any suitable manner to detect a positioning of sound processor apparatus 104 and/or perform a predetermined action with respect to auditory prosthesis system 100 in accordance with the detected positioning of sound processor apparatus 104.

Figure 3:
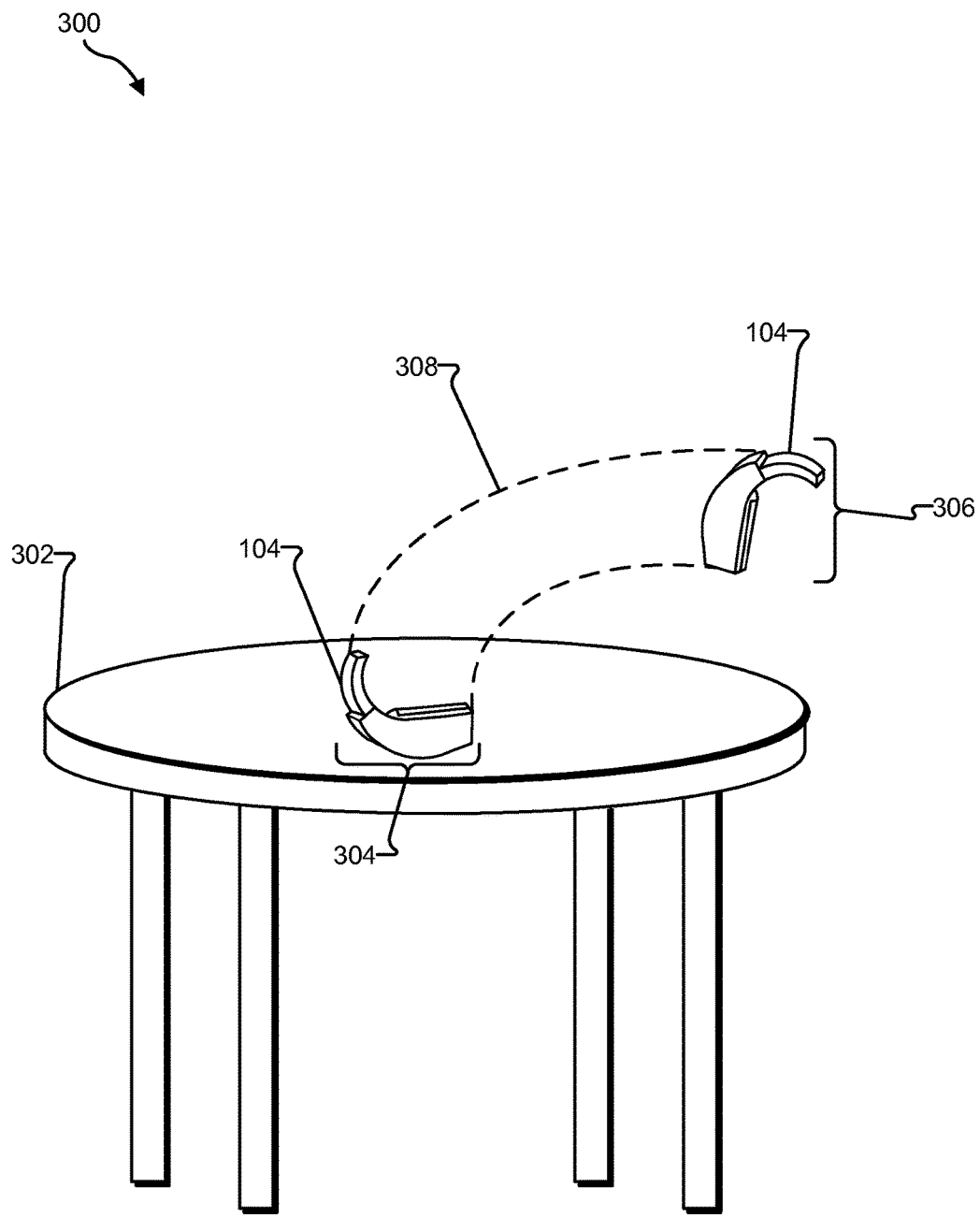
FIG. 3 shows exemplary positionings of the sound processor apparatus of FIG. 2 according to principles described herein.

FIG. 3 shows exemplary positionings of sound processor apparatus 104. As shown in FIG. 3, sound processor apparatus 104 may be positioned on a surface 302 (e.g., a table) in a stationary positioning 304. At some point, sound processor apparatus 104 may experience a change in position 308 (e.g., when a user of sound processor apparatus 104 picks up sound processor apparatus 104 from surface 302 in order to place sound processor apparatus 104 behind the user's ear). During or after change in position 308, sound processor apparatus 104 may be positioned in a mobile positioning 306.

In one implementation, position sensor 204 included within sound processor apparatus 104 may be configured to take periodic measurements used to determine the positioning of sound processor apparatus 104. For example, position sensor 204 may detect and/or measure any magnetic activity, angular momentum, movement, or lack thereof while sound processor apparatus 104 is positioned in stationary positioning 304. In addition, position sensor 204 may generate reference data representative of sound processor apparatus 104 being positioned in stationary positioning 304. Position sensor 204 may then provide the reference data to control module 202 included within sound processor apparatus 104.

By providing the reference data to control module 202, position sensor 204 may enable control module 202 to use the reference data to detect when sound processor apparatus 104 experiences a change in position. For example, at some point, position sensor 204 (e.g., a magnetometer) may detect and/or measure magnetic activity indicative of a change in orientation of sound processor apparatus 104. In another example, position sensor 204 (e.g., a gyroscope) may detect and/or measure angular momentum indicative of a change in orientation of sound processor apparatus 104. Additionally or alternatively, position sensor 204 (e.g., an accelerometer) may detect and/or measure movement indicative of a change in position of sound processor apparatus 104. In addition, position sensor 204 may generate positioning data representative of sound processor apparatus 104 being positioned in mobile positioning 306. Position sensor 204 may then provide the positioning data to control module 202 included within sound processor apparatus 104.

Upon receiving the positioning data from position sensor 204, control module 202 may compare the positioning data with the reference data representative of sound processor apparatus 104 being positioned in stationary positioning 304. Control module 202 may then determine that sound processor apparatus 104 has experienced change in position 308 based at least in part on this comparison of the positioning data and the reference data. In response to determining that sound processor apparatus 104 has experienced change in position 308, control module 202 may perform a predetermined action with respect to auditory prosthesis system 100.

As an example, in the event that control module 202 is operating in an idle mode while positioned in stationary positioning 304, control module 202 may exit the idle mode and begin to operate in an active mode in response to change in position 308. The phrase "idle mode," as used herein, generally refers to any type or form of operating mode that at least partially limits a functionality of an auditory prosthesis system. In contrast, the phrase "active mode," as used herein, generally refers to any type or form of operating mode that facilitates that functionality of the auditory prosthesis system. The active mode, however, may have the adverse effect of decreasing the battery life of sound processor apparatus 104 faster than the idle mode. By exiting the idle mode and beginning to operate in the active mode in response to change in position 308, control module 202 may anticipate and/or address the patient's intent or desire to turn sound processor apparatus 104 to active mode (even without deliberate user input). In some examples, this may facilitate compliance by the patient with Shabbat and/or other religious holidays because the patient does not have to manually turn the sound processor apparatus 104 on.

Figure 4:
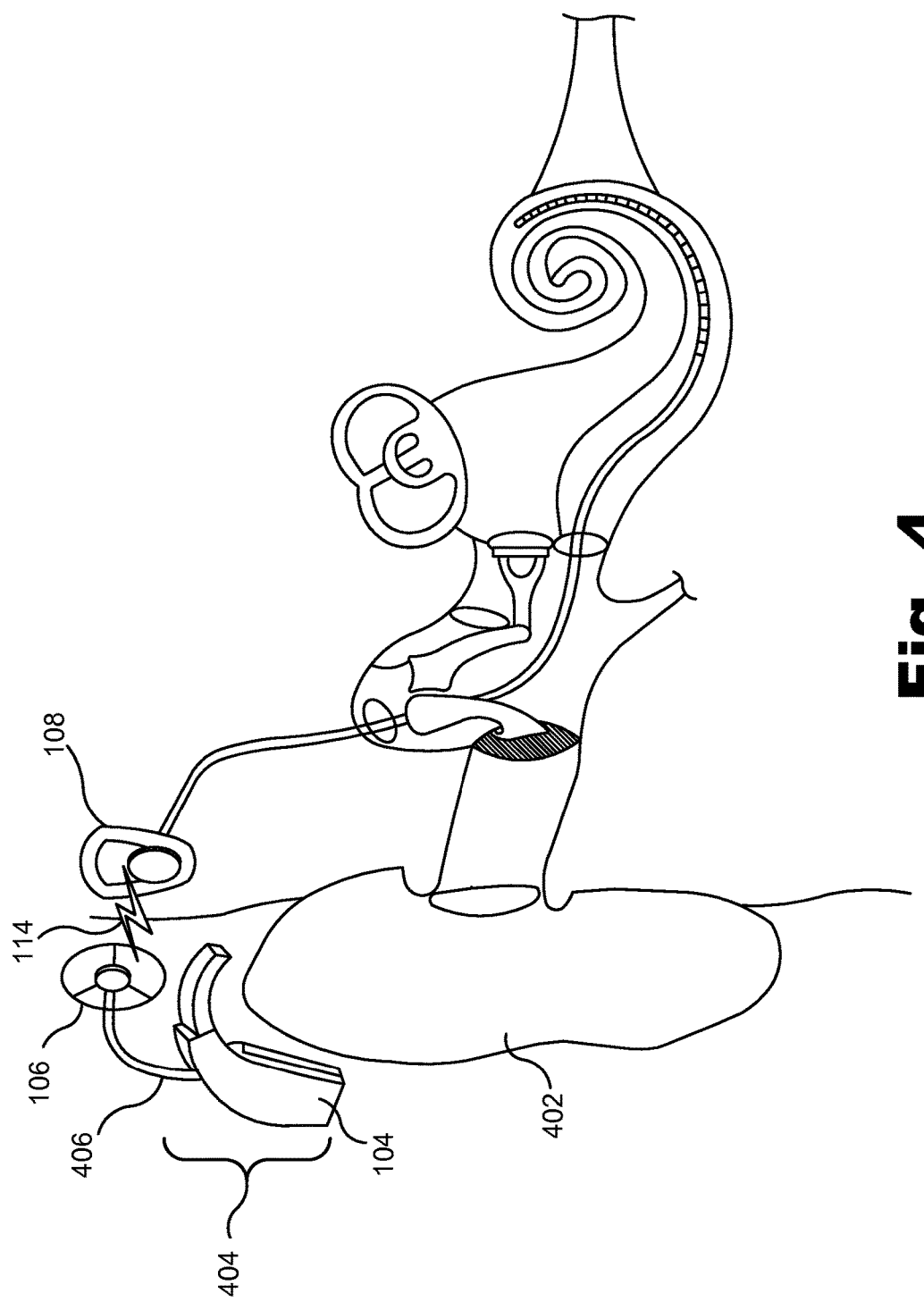
FIG. 4 shows an exemplary preferred positioning of the sound processor apparatus of FIG. 2 according to principles described herein.

FIG. 4 shows an exemplary preferred positioning of sound processor apparatus 104. As shown in FIG. 4, sound processor apparatus 104 may be positioned behind an ear 402 of a patient in a preferred positioning 404. The phrase "preferred positioning," as used herein, generally refers to any type or form of positioning that serves as a preferred reference position and/or orientation of a sound processor apparatus.

In one example, sound processor apparatus 104 may be physically connected and/or communicatively coupled to headpiece 106 by way of a physical communication link 406. In this example, sound processor apparatus 104 may transmit auditory signals and/or control parameters to headpiece 106 by way of physical communication link 406. Headpiece 106 may then transmit the auditory signals and/or control parameters to cochlear implant 108 by way of wireless communication link 114.

In one implementation, control module 202 may obtain and/or store reference data representative of preferred positioning 404 during a fitting session (or at any other time) in which sound processor apparatus 104 is fitted (e.g., by a clinician) to the patient. By obtaining and/or storing the reference data in this manner, control module 202 may be able to use the reference data to detect when sound processor apparatus 104 is positioned in a positioning that differs from preferred positioning 404. For example, at some point, position sensor 204 may detect and/or measure any magnetic activity, angular momentum, movement, or lack thereof indicative of the current position and/or orientation of sound processor apparatus 104. In addition, position sensor 204 may generate positioning data representative of the current position and/or orientation of sound processor apparatus 104. Position sensor 204 may then provide the positioning data to control module 202 included within sound processor apparatus 104.

Upon receiving the positioning data from position sensor 204, control module 202 may compare the positioning data with the reference data representative of the current position and/or orientation of sound processor apparatus 104. Control module 202 may then detect and/or determine a difference between preferred positioning 404 and the detected positioning of sound processor apparatus 104 based at least in part on this comparison of the reference data and the positioning data. For example, control module 202 may detect and/or determine that sound processor apparatus 104 is positioned off-axis by a certain amount relative to preferred positioning 404. In response to detecting and/or determining the difference between preferred positioning 404 and the detected positioning, control module 202 may perform a predetermined action with respect to auditory prosthesis system 100.

As an example, in the event that the detected positioning differs from preferred positioning 404, control module 202 may adjust at least one configuration setting of auditory prosthesis system 100 to compensate for the difference between the detected positioning and the preferred positioning of sound processor apparatus 104. For example, control module 202 may adjust at least one configuration setting that controls a beamforming feature of auditory prosthesis system 100. The phrase "beamforming feature," as used herein, generally refers to any type or form of signal processing technique and/or mechanism that filters noise by applying constructive and/or destructive interference in specific directions relative to the source of the noise. By adjusting the configuration setting that controls the beamforming feature in this manner, control module 202 may potentially improve the performance of auditory prosthesis system 100 and/or provide additional comfort to the patient even without deliberate user input from the patient. In one example, control module 202 may turn the beamforming feature on or off and/or modify the strength of the beamforming feature.

Exemplary configuration settings include, but are not limited to, volume control settings, beamforming settings, program selection settings, operating mode settings (e.g., settings that turn a sound processor apparatus and/or a cochlear implant on or off), audio input source selection settings, fitting settings, noise reduction settings, microphone sensitivity settings, microphone direction settings, pitch settings, timbre settings, sound quality settings, most comfortable current levels ("M levels"), threshold current levels, channel acoustic gain settings, front and backend dynamic range settings, current steering parameters, pulse rate values, pulse width values, frequency settings, amplitude settings, waveform settings, electrode polarity settings (e.g., anode-cathode assignments), location settings (e.g., which electrode pair or electrode group receives the stimulation current), stimulation type settings (e.g., monopolar, bipolar, or tripolar stimulation), burst pattern settings (e.g., burst on time and burst off time), duty cycle parameters, spectral tilt parameters, filter parameters, and dynamic compression parameters.

Figure 5:
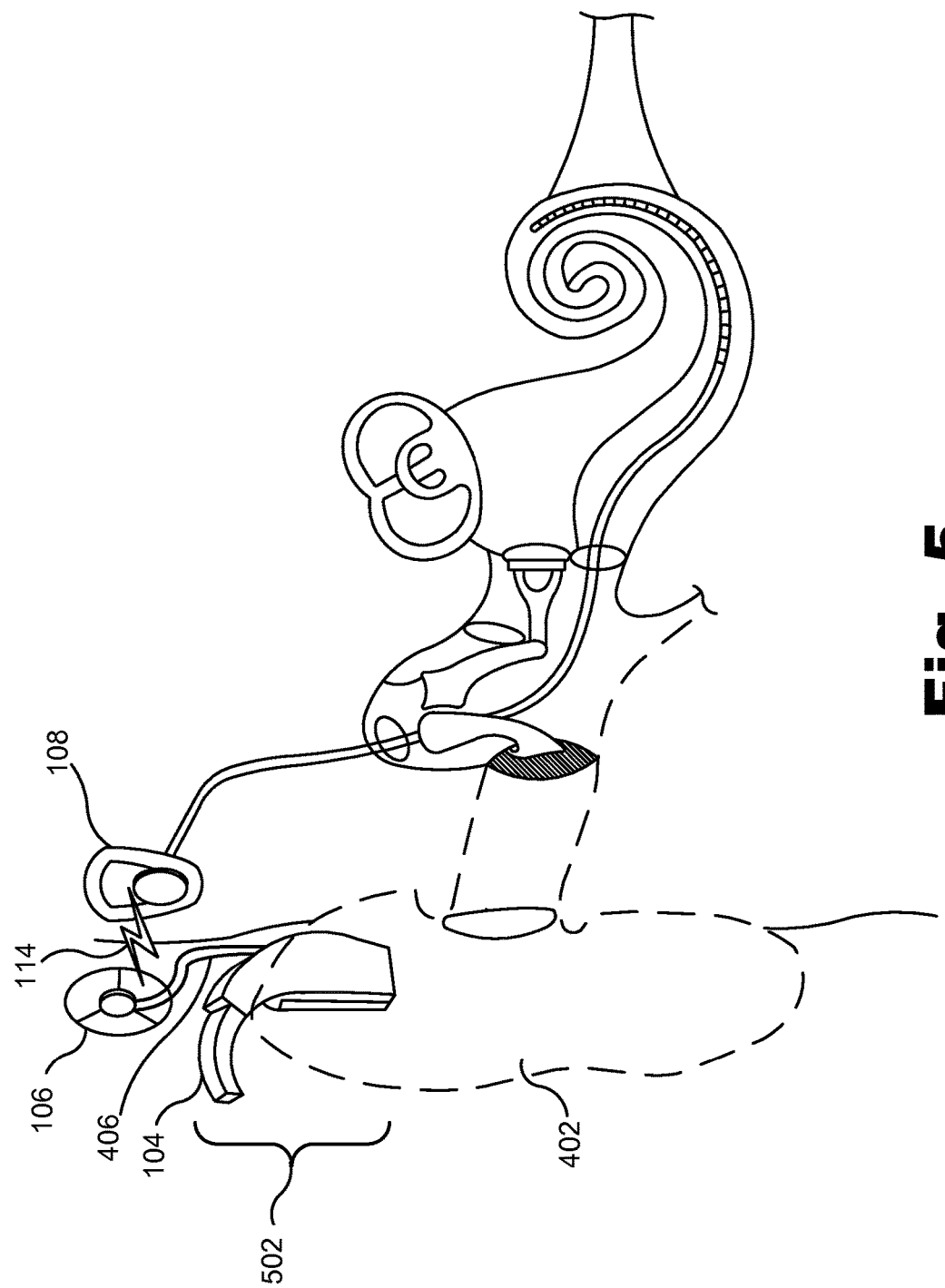
FIG. 5 shows an exemplary detected positioning of the sound processor apparatus of FIG. 2 according to principles described herein.

FIG. 5 shows an exemplary detected positioning of sound processor apparatus 104. As shown in FIG. 5, sound processor apparatus 104 may be positioned on the patient in an off-ear configuration 502 that differs from preferred positioning 404. The phrase "off-ear configuration," as used herein, generally refers to any type or form of positioning and/or configuration in which a sound processor apparatus is worn and/or mounted off of and/or away from a patient's ear. In one example, the patient may position sound processor apparatus 104 in off-ear configuration 502 for increased comfort during a physical activity (e.g., when playing a sport).

Figure 6:
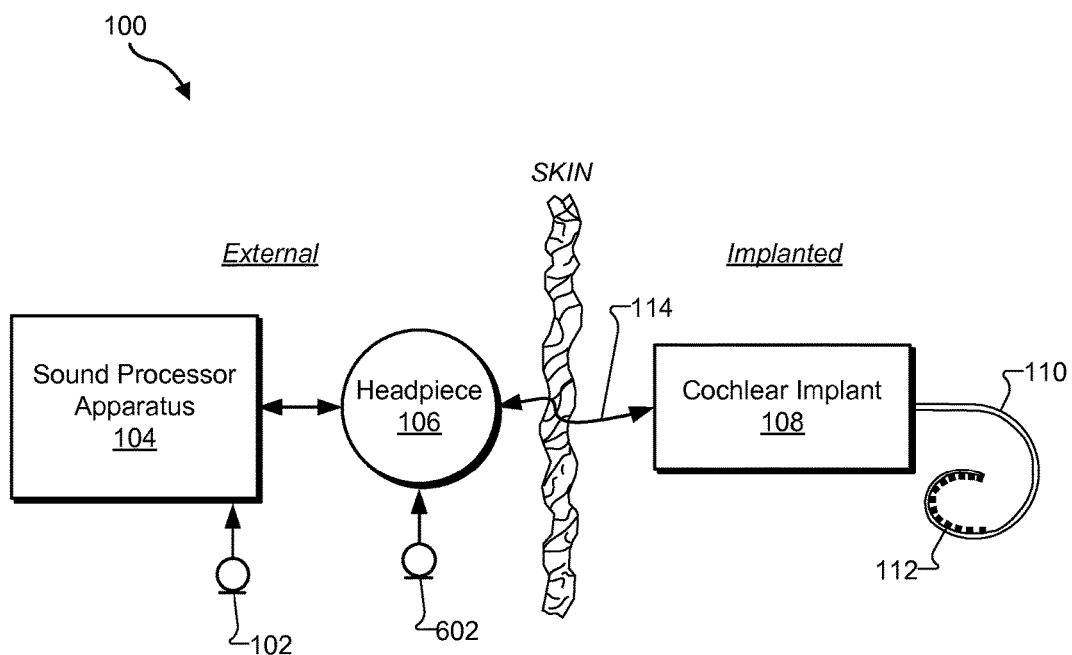
FIG. 6 illustrates an exemplary auditory prosthesis system according to principles described herein.

In the event that sound processor apparatus 104 is positioned in off-ear configuration 502, control module 202 may switch active microphones on auditory prosthesis system 100 to compensate for the difference between preferred positioning 404 and off-ear configuration 502 of sound processor apparatus 104. For example, as shown in FIG. 6, auditory prosthesis system 100 may include microphone 102 associated with sound processor apparatus 104 and a microphone 602 associated with (e.g., included in or connected to) headpiece 106. In one example, microphone 102 may be initially active, and microphone 602 may be initially inactive. In response to detecting and/or determining the difference between preferred positioning 404 and off-ear configuration 502, control module 202 may deactivate microphone 102 and activate microphone 602. By deactivating microphone 102 and activating microphone 602 in this manner, control module 202 may potentially improve the performance of auditory prosthesis system 100 and/or provide additional comfort to the patient even without deliberate user input from the patient.

In one example, control module 202 may detect an active communication link between sound processor apparatus 104 and cochlear implant 108 prior to deactivating microphone 102 and/or activating microphone 602. For example, control module 202 may ensure that sound processor apparatus 104 and cochlear implant 108 are currently able to communicate with each other via physical communication link 406 and wireless communication link 114. In addition, control module 202 may determine that sound processor apparatus 104 is positioned in off-ear configuration 502 based at least in part on active communication link 406 and the difference between preferred positioning 404 and off-ear configuration 502. In other words, control module 202 may deduce and/or infer the patient's intent or desire to use sound processor apparatus 104 while positioned in off-ear configuration 502 since sound processor apparatus 104 is physically connected to (sometimes referred to as being "locked to") active communication link 406. Control module 202 may then initiate the deactivation of microphone 102 and/or the activation of microphone 602 due at least in part to the patient's intent or desire to use sound processor apparatus 104 while positioned in off-ear configuration 502.

Figure 7:
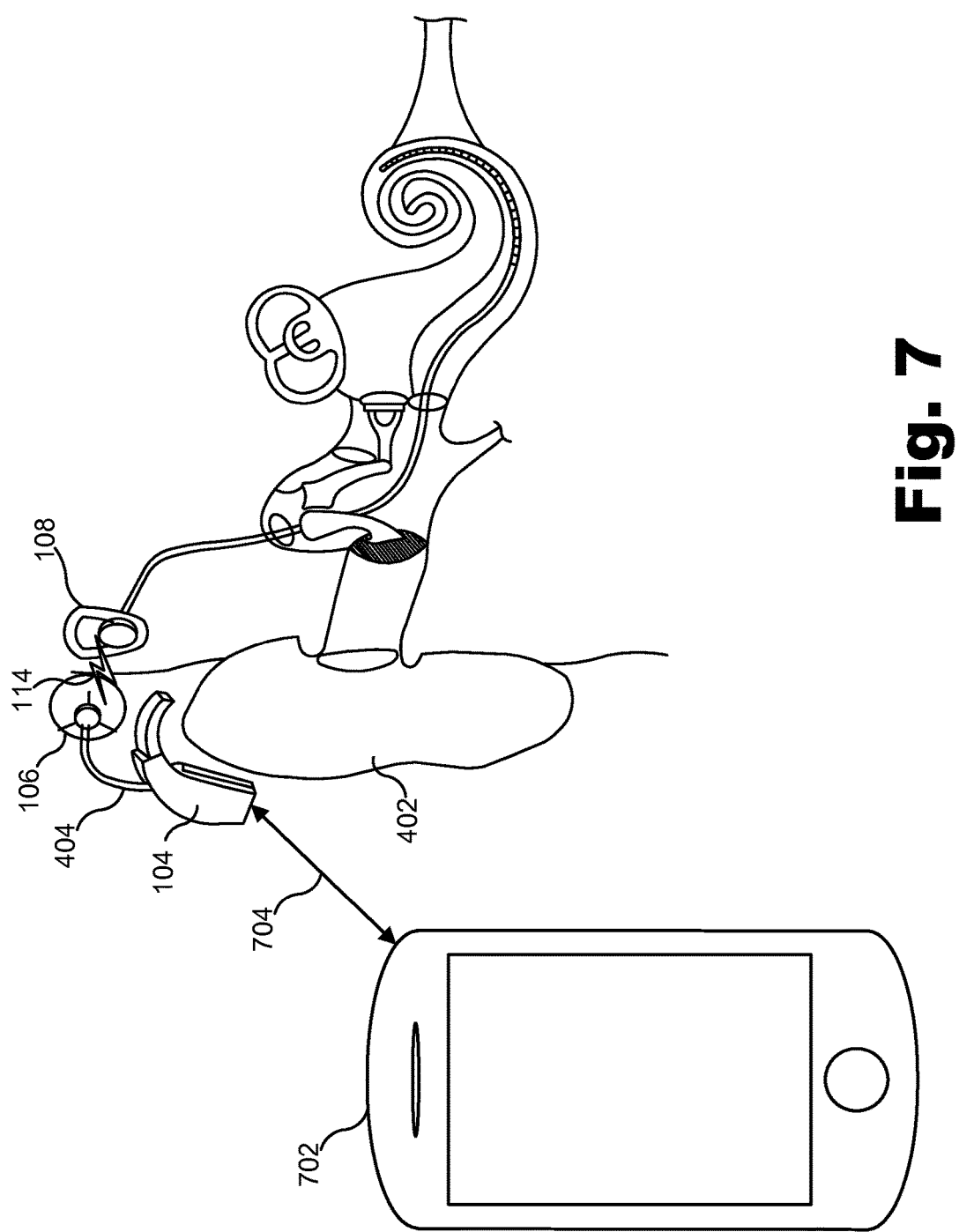
FIG. 7 shows an exemplary detected positioning of the sound processor apparatus of FIG. 2 according to principles described herein.

FIG. 7 shows an exemplary detected positioning of sound processor apparatus 104. As shown in FIG. 7, sound processor apparatus 104 may be mounted external to the patient and positioned physically proximate to a telephone 702 that includes a magnet. Sound processor apparatus 104 may be located at a distance 704 away from telephone 702.

In one example, position sensor 204 may include and/or represent a magnetometer that detects and/or measures certain magnetic activity while sound processor apparatus 104 is positioned physically proximate to telephone 702. For example, the magnetometer may detect and/or measure a relatively strong magnetic field while sound processor apparatus 104 is located at distance 704 away from telephone 702. Additionally or alternatively, the magnetometer may have multiple axes that each yield a substantially saturated response while sound processor apparatus 104 is located at distance 704 away from telephone 702. As a result, the magnetometer may generate magnetic-activity data indicative of sound processor 104 being positioned physically proximate to the magnet included in telephone 702. Position sensor 204 may then provide the magnetic-activity data to control module 202 included within sound processor apparatus 104.

Upon receiving the magnetic-activity data from position sensor 204, control module 202 may compare the magnetic-activity data with reference data representative of sound processor apparatus 104 being positioned physically proximate to a telephone. Control module 202 may then determine that sound processor apparatus 104 is positioned physically proximate to a telephone based at least in part on this comparison of the magnetic-activity data and the reference data. In response to determining that sound processor apparatus 104 is positioned physically proximate to a telephone, control module 202 may direct sound processor apparatus 104 to begin operating in a telephone mode that compensates for sound processor apparatus 104 being physically proximate to the magnet included in telephone 702. The phrase "telephone mode," as used herein, generally refers to any type or form of operating mode in which at least one configuration setting of a sound processor apparatus mounted to a patient is adjusted to potentially improve the performance of the patient's auditory prosthesis system while the patient is on the telephone. For example, control module 202 may automatically enable a telecoil included in sound processing apparatus 104 while sound processing apparatus 104 operates in the telephone mode.

Figure 8:
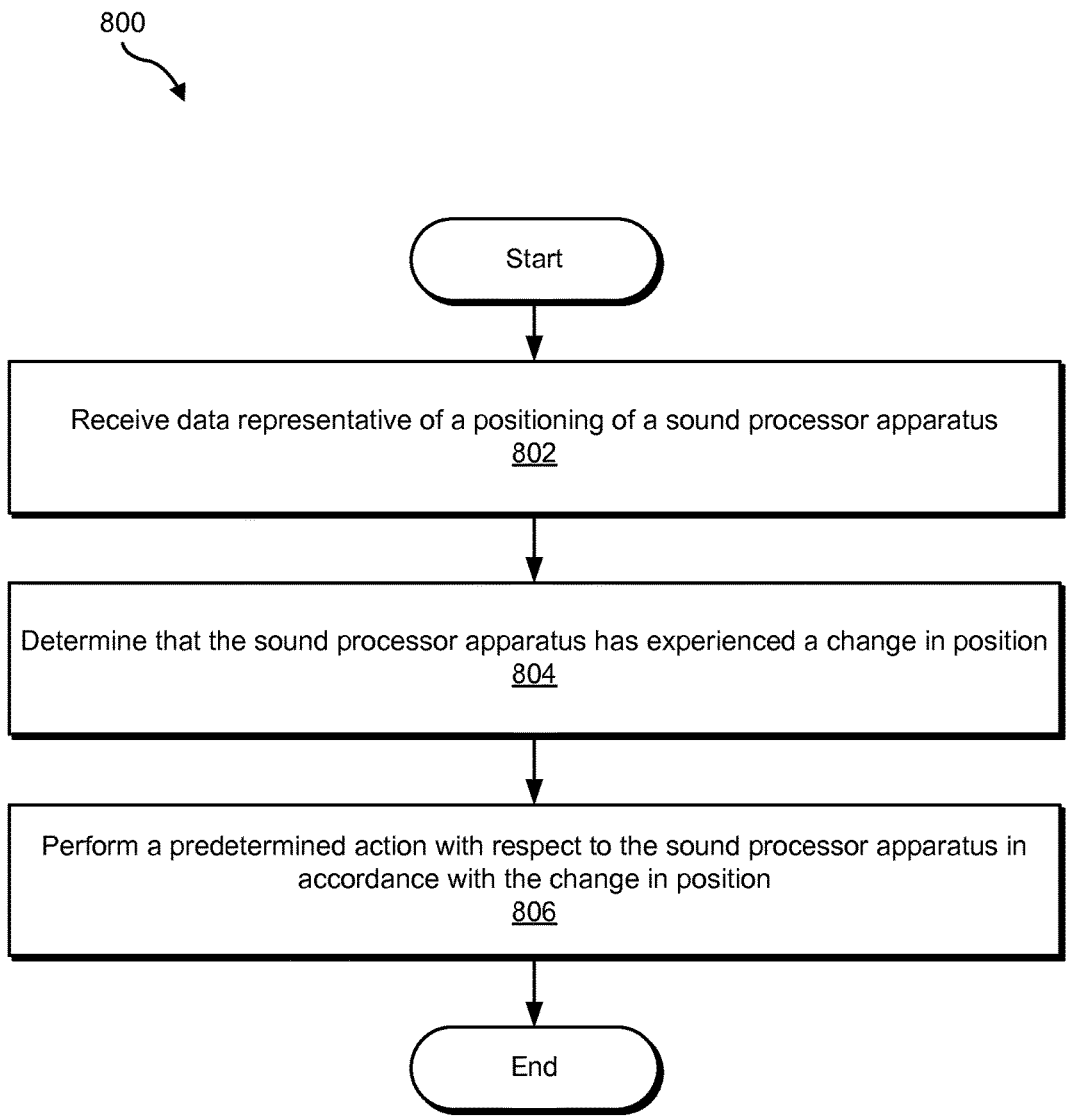
FIG. 8 illustrates an exemplary method according to principles described herein.

FIG. 8 illustrates an exemplary method 800. While FIG. 8 illustrates exemplary steps according to one embodiment, other embodiments may omit, add to, reorder, and/or modify any of the steps shown in FIG. 8. One or more of the steps shown in FIG. 8 may be performed by control module 202 and/or any implementation thereof.

In step 802, a control module included within a sound processor apparatus associated with a patient may receive data representative of a positioning of sound processor apparatus 104. Step 802 may be performed in any of the ways described herein.

In step 804, the control module may determine that the sound processor has experienced a change in position based at least in part on the received data. Step 804 may be performed in any of the ways described herein.

In step 806, the control module may perform a predetermined action with respect to the sound processor apparatus in accordance with the change in position. Step 806 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An auditory prosthesis system comprising:
   a cochlear implant configured to be implanted within a patient;
   a first microphone that is initially active;
   a second microphone that is initially inactive;
   a sound processor apparatus configured to be external to the patient and that includes
      a position sensor configured to detect a positioning of the sound processor apparatus, and
      a control module communicatively coupled to the position sensor and that is configured to
         detect an active communication link between the sound processor apparatus and the cochlear implant;
         access reference data that represents a preferred positioning of the sound processor apparatus;
         receive, from the position sensor, positioning data that represents the detected positioning of the sound processor apparatus;
         determine, based on the reference data and the positioning data, a difference between the preferred positioning and the detected positioning of the sound processor apparatus;
         determine, based on the active communication link and the difference between the preferred positioning and the detected positioning of the sound processor apparatus, that the sound processor apparatus is positioned in an off-ear configuration; and
         initiate, due at least in part to the off-ear configuration, a deactivation of the first microphone and an activation of the second microphone.

2. The method of claim 1,
   wherein the control module is configured to control an operation of the cochlear implant.

3. The auditory prosthesis system of claim 1, wherein the position sensor is configured to detect the positioning of the sound processor apparatus by at least one of:
   detecting magnetic activity indicative of a change in orientation of the sound processor apparatus;

detecting angular momentum indicative of a change in orientation of the sound processor apparatus; and detecting movement indicative of a change in position of the sound processor apparatus.

4. The auditory prosthesis system of claim 1, wherein:
the control module is configured to use the positioning data to determine that the sound processor apparatus has experienced a change in position.

5. The auditory prosthesis system of claim 4, wherein the change in position comprises a change in orientation.

6. The auditory prosthesis system of claim 1, further comprising:
a headpiece removably coupled to the sound processor apparatus and configured to be external to the patient;
wherein the first microphone is included in or connected to the sound processor apparatus and the second microphone is included in the headpiece.

7. The auditory prosthesis system of claim 1, wherein the control module is further configured to adjust at least one configuration setting of the auditory prosthesis system to compensate for the difference between the preferred positioning and the detected positioning of the sound processor apparatus.

8. The auditory prosthesis system of claim 7, wherein the at least one configuration setting controls a beamforming feature of the auditory prosthesis system.

9. The auditory prosthesis system of claim 1, wherein:
the control module is further configured to:
operate in an idle mode that partially limits a functionality of the auditory prosthesis system;
receive, from the position sensor while operating in the idle mode, positioning data that represents the detected positioning of the sound processor apparatus; and
determine, based at least in part on the positioning data, that the sound processor apparatus has experienced a change in position; and
exit, in response to the change in position, the idle mode and begin to operate in an active mode that facilitates full functionality of the auditory prosthesis system.

10. The auditory prosthesis system of claim 1, wherein:
the position sensor comprises a magnetometer;
the control module is further configured to receive, from the magnetometer, magnetic-activity data indicative of the detected positioning of the sound processor apparatus being physically proximate to a magnet included in a telephone; and
direct, due at least in part to the detected positioning of the sound processor apparatus being physically proximate to the magnet included in the telephone, the sound processor apparatus to begin operating in a telephone mode that compensates for the sound processor apparatus being physically proximate to the magnet included in the telephone.

11. The auditory prosthesis system of claim 1, wherein the position sensor comprises at least one of:
a magnetometer;
an accelerometer; and
a gyroscope.

12. An auditory prosthesis system comprising:
a cochlear implant configured to be implanted within a patient;
a plurality of microphones; and
a sound processor apparatus configured to be external to a patient and that includes
a position sensor configured to detect a positioning of the sound processor apparatus, and
a control module communicatively coupled to the position sensor and that is configured to
detect an active communication link between the sound processor apparatus and the cochlear implant;
determine, based on the active communication link and the detected positioning, that the sound processor apparatus is positioned in an off-ear configuration; and
activate or deactivate, based on the determination that the sound processor is positioned in the off-ear configuration, at least one microphone included in the plurality of microphones.

13. The auditory prosthesis system of claim 12, wherein the position sensor is configured to detect the positioning of the sound processor apparatus by at least one of:
detecting magnetic activity indicative of a change in orientation of the sound processor apparatus;
detecting angular momentum indicative of a change in orientation of the sound processor apparatus; and
detecting movement indicative of a change in position of the sound processor apparatus.

14. The auditory prosthesis system of claim 12, wherein:
the position sensor is configured to provide the control module with positioning data representative of the detected positioning; and
the control module is configured to use the positioning data to determine that the sound processor apparatus has experienced a change in position.

15. The auditory prosthesis system of claim 14, wherein the change in position comprises a change in orientation.

16. A method comprising:
detecting, by a control module included within a sound processor apparatus associated with a patient, an active communication link between the sound processor apparatus and a cochlear implant;
receiving, by the control module, data representative of a positioning of the sound processor apparatus;
determining, by the control module based at least in part on the received data and the detecting of the active communication link, that the sound processor apparatus is in an off-ear configuration; and
initiating, based on the determining that the sound processor apparatus is in the off-ear configuration, a deactivation of a first microphone and an activation of a second microphone.

* * * * *